US006417389B1

(12) United States Patent
Studer et al.

(10) Patent No.: US 6,417,389 B1
(45) Date of Patent: Jul. 9, 2002

(54) PROCESS FOR THE PREPARATION OF HPB ESTERS

(75) Inventors: Martin Studer; Peter Herold, both of Basel; Adriano Indolese, Möhlin; Stefan Burckhardt, Gelterkinden, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/647,030

(22) PCT Filed: Mar. 22, 1999

(86) PCT No.: PCT/EP99/01915

§ 371 (c)(1),
(2), (4) Date: Sep. 25, 2000

(87) PCT Pub. No.: WO99/50223

PCT Pub. Date: Oct. 7, 1999

(30) Foreign Application Priority Data

Mar. 31, 1998 (CH) .............................................. 775/98

(51) Int. Cl.$^7$ .......................... C07C 69/76; C07C 69/95; C07C 59/90; C07C 62/32; C07C 65/40
(52) U.S. Cl. .......................... 560/53; 560/123; 560/124; 560/180; 562/463; 562/505; 562/506; 562/508; 562/577
(58) Field of Search ................................. 560/180, 174, 560/53; 562/582, 577, 463, 508

(56) References Cited

U.S. PATENT DOCUMENTS

| 4,329,487 A | 5/1982 | Orito et al. ................... 560/60 |
| 4,336,397 A | * | 6/1982 | Cragoe, Jr. et al. ........... 560/51 |
| 4,739,104 A | * | 4/1988 | Werner et al. ............... 560/174 |
| 4,785,089 A | 11/1988 | Blaser et al. ................ 540/523 |

FOREIGN PATENT DOCUMENTS

EP          206993        12/1986

OTHER PUBLICATIONS

H. U. Blaser et al, Journal of the American Chemical Society, vol. 112, pp. 7048–7050 (Apr. 4, 1990).*
J. L. Margitfalvi, Chemical Industry, "On the Role of Modifier–Substrate Interactions in Different Heterogeneous Catalytic Asymmetric Hydrogenation Reactions", pp. 189–200 (1995).*
Baraldi et al, Tetrahedron Letters, "Regio–and Enantioselective Bioreduction of Ethyl 2,4–Dioxoalkanoates and gamma–Keto–alpha–Enamino Esters with Fermenting Baker's Yeast" pp. 2871–2874 (1992).*
Groggins, Processes in Organic Synthesis p. 579 (1958).*
H. U. Blaser et al., Journal of Molecular Catalysis, 68, (1991), pp. 215–222.
H. U. Blaser et al., Applied Catalysis, 52, (1989), pp. 19–32.
G. Casey, Tetrahedron Letters, vol. 33, No. 52, pp. 8159–8162, (1992).
A. Pfaltz et al., Topics in Catalysis, 4, (1997), pp. 229–239.
Beilstein Information Service; File: XFIRE, XP002108319 see BRN: 7767902, 7643984, 4695084, 3590943, 3590942.

* cited by examiner

*Primary Examiner*—Gary Geist
*Assistant Examiner*—Zachary C. Tucker
(74) *Attorney, Agent, or Firm*—Kevin T. Mansfield

(57) ABSTRACT

This invention relates to a novel advantageous process for the stereoselective preparation of 2-hydroxy-4-phenylbutyrates (HPB esters) and of their precursors. This is done by starting from readily accessible α-unsaturated α-hydroxy-γ-keto esters which can be prepared by Claisen condensation.

5 Claims, No Drawings

PROCESS FOR THE PREPARATION OF HPB ESTERS

The present invention relates to a novel, inventive process for the stereoselective preparation of 2-hydroxybutyrates, in particular of 2-hydroxy-4-phenylbutyrates (HPB ester), and of their precursors.

HPB esters of formula

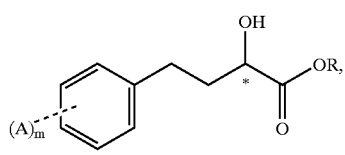

(I)

wherein A is substituents, m is an integer from 0 to 5 and R is an ester group and wherein the symbol * indicates a chiral centre, are important intermediates for the preparation of pharmacologically effective ACE inhibitors (ACE: angiotensin converting enzyme) which have the following shared structural feature:

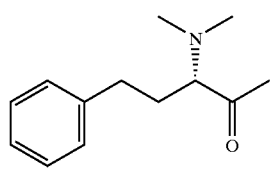

ACE inhibitors belong to the active ingredient group of the antihypertensives and effect after oral administration a competitive inhibition of the so-called angiotensin converting enzyme and thus a lowering of the blood pressure. A particularly preferred HPB ester has the R-configuration.

An important active ingredient is 3-[(1-(ethoxycarbonyl)-3-phenyl-(1 S)-propyl)amino]-2,3,4,5-tetrahydro2-oxo-1H-1-(3S)-benzazepine-1-acetic acid hydrochloride which is known under the INN name benazepril HCl and which is commercially available in diverse oral forms of presentation, e.g. tablets, under the registered trademark Cibacen® (trademark of Novartis AG, Basel Switzerland). HPB esters can furthermore be used as intermediates for the preparation of other known ACE inhibitors, for example enalapril, cilazapril, spirapril, quinapril, ramipril or lisinopril (INN names). HPB esters can also be used for the synthesis of different types of insecticides.

Many different methods are known for preparing R-configurated HPB esters, for example reductions with micro-organisms or enzymes, enantioselective hydrogenations with homogeneous or heterogeneous catalysts, diastereoselective hydrogenations, reduction with hydrides, reactions with so-called chiral building blocks, enzymatic racemate resolution or racemate resolutions on chiral substrates, or inversion of the S-HPB ester.

These methods are disadvantageous for various reasons, such as
- use of costly educts, e.g. 2-oxo-4-phenylbutyric acid
- reaction at low concentrations (general problem in the case of biological or enzymatic processes)
- high process costs in the case of homogeneous catalysis
- maximum yield of only 50% in the case of racemate resolutions.

This invention has for its object to enantioselectively synthesise 2-hydroxybutyrates of the desired configuration, in particular HPB esters, starting from starting materials which are obtainable by simple synthesis. In the narrower meaning, this invention has for its object to enantioselectively synthesise HPB esters having the desired R-configuration without the losses necessitated by racemate resolution.

European patent application No. 206 993 describes the preparation of HPB esters through heterogeneous catalytic reduction with platinum catalysts of α-keto esters of formula

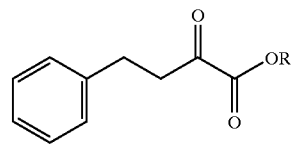

The hydrogenation can be carried out enantioselectively in the presence of a chiral modifier, e.g. cinchonidine, so that the desired R-form is predominantly obtained. In spite of this possibility, this process is disadvantageous because the α-keto ester must be prepared before-hand, the synthesis of which over several process steps is complicated.

Surprisingly, it has been found that starting from the α,γ-diketo esters of formula

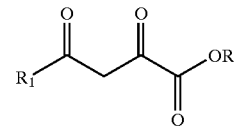

($R_1$ e.g. phenyl) which are accessible by simple Claisen condensation, or from their tautomeric α-unsaturated α-hydroxy-γ-keto esters;

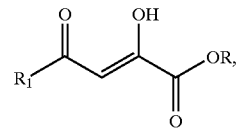

an α-hydroxy-γ-keto ester is obtained by enantioselective hydrogenation in the presence of a suitable chiral modifier, which α-hydroxy-γ-keto ester can be crystallised in enantiomerically pure form, for example in the desired R-configuration, in high optical yield and which can be converted to 2-hydroxybutyrate in a subsequent catalytic hydrogenation.

This invention relates to a process for the preparation of compounds of formulae

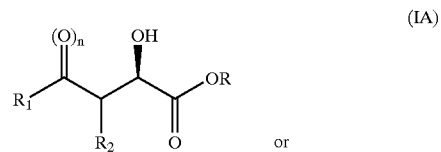

(IA)

or

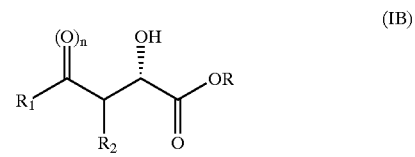

(IB)

wherein

R is hydrogen or an ester group, $R_1$ is hydroxy, etherified hydroxy, $C_1$–$C_8$alkyl, $C_3$–$C_8$cycloalkyl, phenyl or phenyl which is substituted by 1 to 5 substituents, $R_2$ is hydrogen or $C_1$–$C_4$alkyl and n is 0 or 1, which process comprises enantioselectively hydrogenating an α,γ-diketo ester of formula

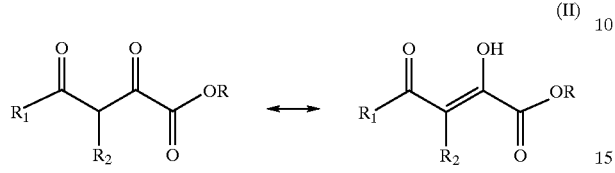
(II)

wherein R, $R_1$ and $R_2$ have the cited meanings, or the tautomer thereof, with platinum as catalyst in the presence of a cinchona alkaloid as chiral modifier and, if desired, hydrogenating for the preparation of a compound (IA) or (IB), wherein n is 0, one of the obtainable compounds of formulae

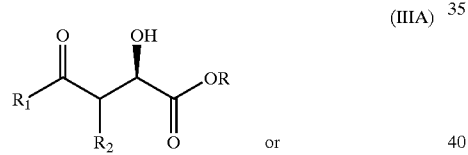
(IIIA)

or

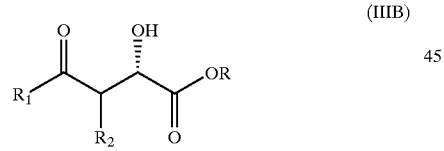
(IIIB)

having the desired configuration with palladium as catalyst.

A preferred embodiment of this invention relates to a process for the preparation of a compound (IA) or (IB), wherein R is e.g. hydrogen, $C_1$–$C_4$alkyl, preferably methyl or ethyl. $R_1$ is hydroxy, etherified hydroxy, for example $C_1$–$C_4$alkoxy, such as methoxy or ethoxy, $C_1$–$C_4$alkyl, for example methyl, ethyl, n-propyl, isopropyl or n-, iso- or tert-butyl, phenyl or phenyl substituted by 1-5 substituents A. $R_2$ is hydrogen or $C_1$–$C_4$alkyl, preferably methyl and n 0 or 1.

A particularly preferred embodiment of this invention relates to a process for the preparation of compounds of formulae

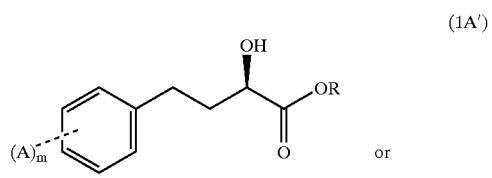
(1A')

or

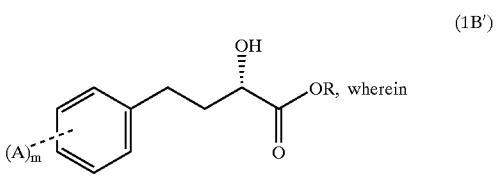
(1B'), wherein

A is substituents, m is an integer from 0 to 5 and

R is an ester group, which process comprises enantioselectively hydrogenating an α,γ-diketo ester of formula

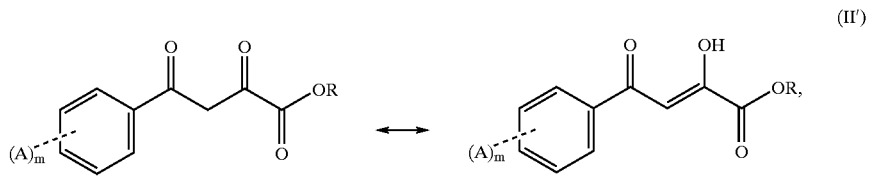
(II')

wherein A, m and R have the cited meanings, or the tautomer thereof, with platinum as catalyst in the presence of a cinchona alkaloid as chiral modifier and hydrogenating one of the obtainable compounds of formulae

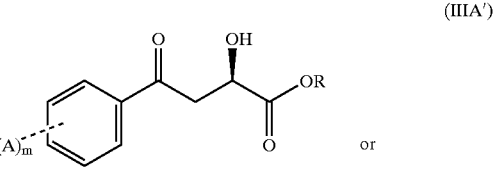
(IIIA')

or

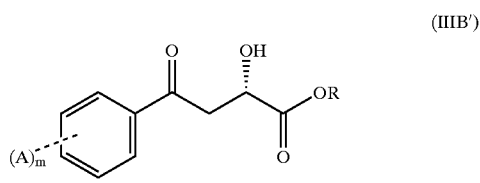
(IIIB')

having the desired configuration with palladium as catalyst.

The symbols, terms and denotations used in the description of this invention are preferably defined as follows:

the symbols
and

in the structural formulae mean that a predominant number of the molecules has the indicated stereochemical configuration at the chiral centre which, according to the nomenclature rules (R,S-nomenclature) of Cahn, Ingold and Prelog, has the denotation R or S.

In compounds (IA) and (IB) the ester group R is preferably a saturated hydrocarbon radical, in particular $C_1$–$C_{20}$alkyl, $C_3$–$C_{12}$cycloalkyl, $C_2$–$C_{11}$heterocycloalkyl, $C_6$–$C_{16}$aryl, $C_1$–$C_1$–$C_{15}$heteroaryl or $C_7$–$C_{16}$aralkyl, which can be substituted by one or more than one substituent selected from the group consisting of $C_1$–$C_6$alkyl, $C_1$–$C_6$alkoxy, $C_1$–$C_6$haloalkyl, $C_6$–$C_{16}$aryl, carboxy, $C_1$–$C_4$alkoxycarbonyl, $C_1$–$C_4$alkanoyl, —$SO_3^-$, ammonium and halogen.

Examples of $C_1$–$C_{20}$alkyl are methyl, ethyl, n-propyl, isopropyl, n-butyl, isobutyl, tert-butyl and the isomers of pentyl, hexyl, heptyl, octyl, nonyl, decyl, undecyl and dodecyl. An example of aryl-substituted alkyl is benzyl.

Some examples of $C_3$–$C_{12}$cycloalkyl are cyclopropyl, cyclopentyl and cyclohexyl. Examples of substituted cycloalkyl are cyclopentyl and cyclohexyl which are substituted by methyl, dimethyl, trimethyl, methoxy, dimethoxy, trimethoxy, trifluoromethyl, bis-trifluoromethyl and tris-trifluoromethyl.

$C_2$–$C_{11}$heterocycloalkyl preferably contains one or two, and $C_1$–$C_{15}$heteroaryl one to four, heteroatoms, which are selected from the group consisting of oxygen, sulfur and nitrogen. Some examples of heierocycloalkyl are tetrahydrofuryl, pyrrolidinyl, piperazinyl and tetrahydrothienyl. Some examples of heteroaryl are furyl, thienyl, pyrrolyl, pyridyl and pyrimidinyl.

Examples of $C_6$–$C_{16}$aryl are phenyl and naphthyl. Examples of substituted aryl are phenyl substituted by methyl, dimethyl, trimethyl, methoxy, dimethoxy, trimethoxy, trifluoromethyl, bis-trifluoromethyl or tris-trifluoromethyl. One example of $C_7$–$C_{16}$aralkyl is benzyl. Examples of substituted aralkyl are benzyl substituted by methyl, dimethyl, trimethyl, methoxy, dimethoxy, trimethoxy, trifluoromethyl, bis-trifluoromethyl or tris-trifluoromethyl.

Heterocycloalkyl preferably contains one or two, and heteroaryl one to four, heteroatoms, which are selected from the group consisting of oxygen, sulfur and nitrogen. Some examples of heterocycloalkyl are tetrahydrofuryl, pyrrolidinyl, piperazinyl and tetrahydrothienyl. Some examples of heteroaryl are furyl, thienyl, pyrrolyl, pyridyl and pyrimidinyl.

A saturated hydrocarbon radical R is preferably $C_1$–$C_7$alkyl, for example methyl, ethyl, n-propyl, n-butyl, isobutyl or tert-butyl.

Suitable substituents A of phenyl are typically $C_1$–$C_7$alkyl, for example methyl, ethyl, n-propyl, n-butyl, isobutyl, tert-butyl or neopentyl, $C_1$–$C_7$alkoxy, for example methoxy, ethoxy or tert-butoxy, $C_1$–$C_4$alkanoyl, for example acetyl or propionyl, $C_1$–$C_4$alkanoyloxy, for example acetoxy, cyanogen, halogen, for example fluoro, chloro, bromo or iodo, hydroxy, carboxy, $C_1$–$C_4$alkoxycarbonyl, for example methoxy- or ethoxycarbonyl, $C_1$–$C_7$alkylenedioxy, for example ethylenedioxy, amino, $C_1$–$C_4$alkylamino, for example methyl- or ethylamino, di($C_1$–$C_7$alkyl)amino, for example dimethyl- or diethylamino, $C_1$–$C_4$alkanoylamino, for example acetylamino, carbamoyl, $C_1$–$C_4$alkylcarbamoyl, for example methylcarbamoyl, di($C_1$–$C_7$alkyl)carbamoyl, for example dimethylcarbamoyl, $C_1$–$C_4$alkanesulfonylamino, for example mesylamino or trifluoromethanesulfonylamino, arenesulfonylamino, for example benzenesulfonylamino or p-toluenesulfonylamino, sulfo, sulfamoyl, $C_1$–$C_4$alkylsulfamoyl, for example methylsulfamoyl, di($C_1$–$C_7$alkyl)sulfamoyl, for example dimethylsulfamoyl, halogen-$C_1$–$C_7$alkyl, for example trifluoromethyl, hydroxy-$C_1$–$C_7$alkyl, for example hydroxymethyl or 1- or 2-hydroxethyl, or amino-$C_1$–$C_7$alkyl, for example aminomethyl or 1- or 2-aminoethyl.

Two substituents A can form bivalent, bridge-like $C_2$–$C_6$alkylene, $C_4$–$C_8$alkyldiylidene or $C_4$–$C_8$alkenyldiylidene groups, preferably butanediylidene, in particular 2-butendiylidene, which are bound with the phenyl ring to two adjacent carbon atoms and which form with these carbon atoms a bicycle, preferably a condensed biphenyl ring, for example the naphthyl group, which bicycle can be substituted by the cited functional groups or substituents.

Functional groups, for example amino, hydroxy, carboxy or sulfo, can be protected by suitable protective groups, for example trimethylsilyl, tert-butyl, p-nitrobenzyl, phthaloyl etc.

Salt-forming groups, for example carboxy or sulfo, can be present in free form or in salt form, for example in the form of sodium salt. Amino groups and substituted amino groups can be present in free form or in the form of acid addition salts, such as hydrochloride.

The index m is preferably 0, 1, 2 or 3.

In a preferred embodiment of the process, a compound (I A') or (I B') is prepared, wherein m is 0 and R is $C_1$–$C_4$alkyl.

In a particularly preferred embodiment of the process, a compound (I A') is prepared, wherein m is 0 and R is ethyl.

A chiral modifier contains a basic nitrogen atom which is close to one or several chiral centres, which in turn are bound to a bicyclic aromatic compound. Suitable chiral modifiers are described by *A. Pfaltz and T. Heinz in Topics in Catalysis* 4(1997) 229-239. Preferred modifiers are cinchona alkaloids which are known under this name and which belong to the group of quinoline vegetable bases which can be isolated mainly from the bark of trees of the cinchona and remijia family. This definition embraces in particular the alkaloids (−)-quinine, (+)-quinidine, (+)-cinchonine and (−)-cinchonidine. The use of (−)-quinine and (−)-cinchonidine results in compounds (III) in the R-form (III A), and the use of (+)-quinidine and (+)-cinchonine results in compounds (III) in the S-form (III B). It is preferred to use (−)-cinchonidine and derivatives thereof.

In a particularly preferred embodiment of this invention, the chiral modifiers used for the preparation of the R-form (III A) are derivatives of the (−)-cinchonidine of formula

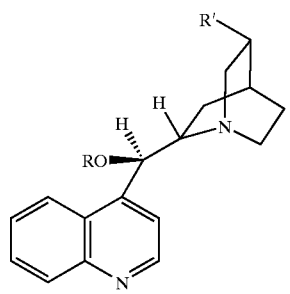

(IV)

wherein
R is hydrogen, methyl, acetyl, lactoyl or lactoyl etherified by benzyl, and
R' is ethyl or hydroxymethyl.

Compound (IV) wherein R is hydrogen and R' is ethyl is known under the name 10,11-dihydrocinchonidine (HCd), and compound (IV) wherein R is methyl and R' is ethyl is known under the name O-methoxy-10,11-dihydrocinchonidine (MeOHCd), and compound (IV) wherein R is hydrogen and R' is hydroxymethyl is known under the name norcinchol.

In a preferred embodiment of the process, the chiral modifier (IV) is 10,11-dihydrocinchonidine (HCd).

The enantioselective reduction is carried out in a manner known per se. The platinum catalysts used can be in the form of so-called polymer-stabilised colloidal metal clusters, such as those described by X. Zuo et al. in *Tetrahedron Letter* 39(1998) 1941–1944, or are preferably applied to suitable substrates. Examples of suitable substrates are carbon, aluminium oxide, silicium dioxide, $Cr_2O_3$, zirconium dioxide, zinc oxide, calcium oxide, magnesium oxide, barium sulfate, calcium carbonate or aluminium phosphate. Aluminium oxide is preferred. The catalysts are activated in a manner known per se with hydrogen at about 200 to 400° C. and are then modified with the solution of cinchona alkaloid and impregnated, and/or the cinchona alkaloid is added direct during reduction.

Hydrogenation is carried out in the presence of water or of an organic solvent. It is preferred to use polar and non-polar aprotic or polar protic solvents or mixtures thereof.

Examples of suitable non-polar aprotic solvents are hydrocarbons, for example aliphatic hydrocarbons, e.g. hexane, heptane or petroleum ether, cycloaliphatic hydrocarbons, for example cyclohexane or methylcyclohexane, aromatic hydrocarbons, for example benzene, toluene or xylene.

Examples of suitable polar aprotic solvents are ethers, for example aliphatic ethers, e.g. diisopropyl ether, 1,2-diethoxyethane or tert-butylmethyl ether, cyclic ethers, for example tetrahydrofuran or dioxane, amides, for example dimethylformamide or N-methylpyrrolidone. Particularly suitable are ethers, in particular tetrahydrofuran.

Examples of suitable polar protic solvents are alcohols, for example ethanol or n-butanol.

The process may preferably be carried out in the liquid phase batchwise or continuously, preferably with a catalyst suspension as liquid-phase hydrogenation or in a bubble column or with a formated catalyst in a trickle bed. The reaction can also be carried out in the gas phase with a powdered catalyst in a fluidised bed or with a formulated catalyst in a fixed bed.

The hydrogenation can be carried out in a wide range of temperatures. Advantageous temperatures have been found to be those in the range from room temperature to about 100° C., preferably from 20° to about 50° C.

The hydrogen pressure can vary within a wide range during hydrogenation, for example from 1–200, preferably from 5–100, more preferably from 10–60 bar. Which hydrogen pressure is used depends essentially on the hydrogenation plant available.

The reaction time can vary within wide limits and depends on the catalyst used, on the hydrogen pressure, on the reaction temperature and on the plant used. It can be, for example, in the range from half an hour to 24 hours. Advantageous reaction times are those from about half an hour to two hours.

The isolation of the reaction products is carried out by known methods and is illustrated in the Examples. After separating the catalyst and removing the solvent, the customary separation processes may follow, for example preparative thin-layer chromatography, preparative HPLC, preparative gas chromatography and the like. In a particularly preferred embodiment of this invention, the R-compound (III A) is crystallised from a suitable solvent. Diisopropyl ether has been found to be a particularly advantageous solvent. The R-compound (III A) is obtained in a special optical purity ee of up to 99% by crystallisation from this solvent.

The subsequent hydrogenation of the compound (III A) or (III B) with palladium as catalyst, e.g. palladium (black) or palladium chloride, is carried out in a manner known per se. The palladium catalysts used are applied to substrates. In a preferred embodiment of this invention palladium is applied to carbon.

The solvents used are polar protic solvents, for example ethanol. If required, acid assistants are added, for example organic mono- or polyvalent acids containing more than two carbon atoms, for example acetic acid, propionic acid or malonic acid, mineral acids, for example hydrogen chloride or sulfuric acid, so-called Lewis acids, for example boron trifluoride, or so-called solid acids, such as zeolites or Nafion® and/or dehydrating agents, for example sodiun sulfate.

The isolation of the reaction products is carried out by known methods and is described in the Examples. After separating the catalyst and removing the solvent, the customary separation processes may follow, for example preparative thin-layer chromatography, preparative HPLC, preparative gas chromatography and the like.

Compounds of formulae

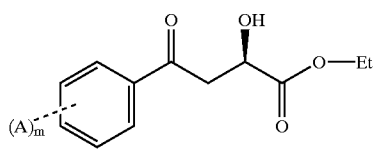

(IIIA')

and

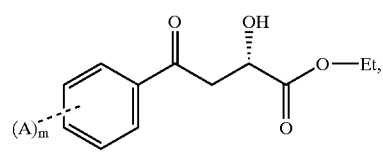

(IIIB')

wherein A is substituents, m is an integer from 0 to 5 and Et is ethyl, are novel and are also a subject matter of this invention.

A particularly preferred embodiment of this invention is the compound (R)-2-hydroxy-4-oxo-4-phenylbutyric acid ethyl ester.

Enantiomerically pure compounds of formula

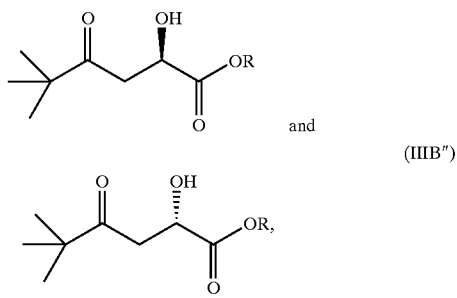

wherein R is an ester group with the exception of methyl, are novel and are also a subject matter of this invention.

Enantiomerically pure compounds of formula (III A″) or (III B″), wherein R is hydrogen or methyl, are known (CAS 61689–31–4 and 61689–32–5).

A particularly preferred subject matter of this invention is the compound 5,5-dimethyl-(R)-2-hydroxy-4-oxohexanoic acid ethyl ester.

This invention also relates to the use of compound I A′ having an R-configuration for the preparation of compounds comprising the group

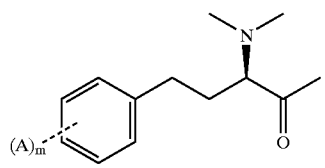

as component, and correspondingly to the use of compound I B′ having an S-configuration for the preparation of compounds comprising the group

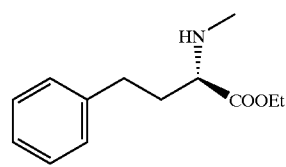

as component.

Compounds (IA′), in particular, are valuable intermediates for the preparation of ACE-inhibitors or of their further precursors. In a number of effective ACE-inhibitors, see e.g. EP-A-50 850 and EP-A-72 352, the pharmacophoric group is defined as partial structure

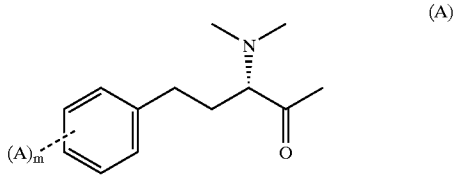

having an S-configuration. This group is present in known ACE-inhibitors called benazepril, enalapril, cilazapril, spirapril, quinapril, ramipril and lisinopril. The pharmacological effect of ACE-inhibitors is described in numerous textbooks of pharmacology and pharmaceutical chemistry, inter alia in *Helwig/Otto, Arzneimittel*, Vol. I, 30-127–131, *Wissenschaftliche Verlagsgesellschaft mbH Stuttgart* 1995.

The introduction of the amino group, see the above partial structure, is carried out by known processes, for example by esterification of the HPB ester at the hydroxyl group via a sulfonyl group, for example trifluoromethanesulfonyl, so that this hydroxyl group is substituted by a leaving group. This derivative is then reacted, with inversion, with an amino compound which comprises the group —NH—R (R=additional substituents characterising the ACE-inhibitor), so that an S-configurated compound is obtained. Further processing to pharmacologically active ACE-inhibitors is described in EP-A-206 993. In detail, these further processing steps have the advantage that the compounds (I) can be reacted in the respective desired configuration (IA) or (IB) with amino compounds without any disadvantageous racemisation or without the occurrence of elimination products.

The further processing of the HPB esters to insecticides of suitable structure can be carried out by the method described in the British patent specification No. 1 014 243.

Compounds (I A) and (IB), wherein $R_1$ is hydroxy, etherified hydroxy or $C_1$–$C_4$alkyl, $R_2$ is hydrogen or $C_1$–$C_4$alkyl and n is 0 or 1, are valuable starting materials for the synthesis, e.g. D-maleic acid having an "unnatural" configuration, or intermediates for the synthesis of correspondingly configurated amino acids, or can be used as ligand formers in complex chemistry, in particular the diketones of the compounds (I A) or (I B), wherein n is 1.

The preparation of α,γ-diketo esters or of their tautomeric α-unsaturated α-hydroxy-γ-keto esters (II) can be carried out in analogy to the classic method described by *C. Beyer and L. Claisen in Berichte*, Vol. XX (1887) 2178–2188.

EXAMPLE 1

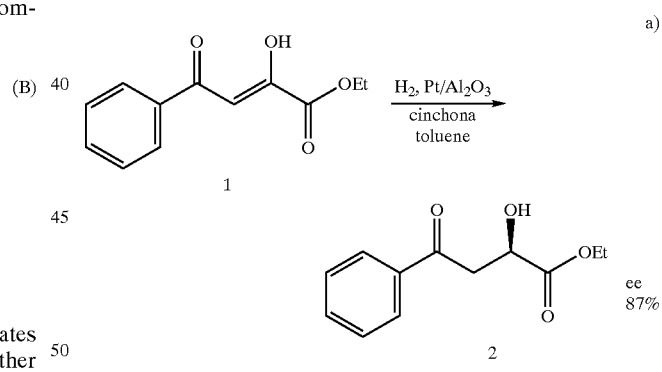

2.0 g of 1 (MG 220.24; 9.08 mmol) are dissolved with 30 ml of toluene in a 50 ml stainless steel autoclave, equipped with double-walled jacket, magnetic stirrer and baffles. This solution is charged with 50 mg of 5% Pt/Al$_2$O$_3$ (Engelhard 4759, pretreated for 2 h in H$_2$ at 400° C.) and 5 mg of 10,11-dihydrocinchonidine. The autoclave is closed and rinsed twice with argon and twice with hydrogen. Subsequently, 60 bar H$_2$ are forced in and the reaction is started by stirring with the magnetic stirrer (1200 rpm). During the reaction the temperature is kept at 25° C. (thermostat) and the pressure at 60 bar H$_2$. Hydrogen uptake is completed after a reaction time of 160 min. After relaxation, the autoclave is rinsed again with argon. The reaction mixture is filtered and concentrated by evaporation, giving 1.97 g of 2 [MG 222.24; yield: 98%; purity: >97%

(HPLC, NMR); ee-product=87% (HPLC); MS: M+: 222; 1-H NMR (CDCl$_3$, TMS): 7.95 (d, 2H), 7.60 (dd, 1H), 7.45 (dd, 2H), 4.65 (m, 1H), 4.25 (q, 2H), 3.30–3.60 (m, 3H), 1.30 (t, 3H); 13-C NMR (CDCl$_3$, TMS), 198, 174, 136, 134, 129, 128, 67, 62, 42, 14 ppm].

b) The hydroxy ester 2 (73.85 g; 0.332 mol; ee=76%) is dissolved in 220 ml of diisopropyl ether. After adding some seeding crystals, the solution is cooled in a water bath to 15° C. The crystallisation starts after 5 min. The mixture is stirred for another 30 min and the crystallisation is ended by stirring for 30 min at 10° C. and for 2 hours at 0° C. The product is collected by filtration, washed once with 70 ml of ice-cold diisopropyl ether and dried overnight under vacuum at room temperature. Yield: 47.14 g (63.8%, yellowish crystals); melting point (not corrected): 37.0° C.; purity ee-product (HPLC,OD, hexane/ethanol/TFA 970 ml/30 ml/0.4 ml): 99%.

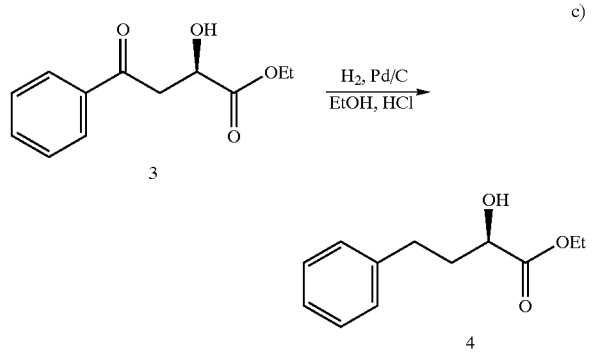

A solution of hydroxy ester 3 (46.0 g, 0.20 mol; ee=99%) in 170 ml of ethanol is charged with 5% Pd/C (460 mg), HCl in ethanol (12% w/v; 18.7 ml). The mixture is shaken at room temperature and hydrogenated for 5½ hours at 1 bar H$_2$ in a glass shaker. The catalyst is removed by filtration and the solvent is removed by evaporation. The yellowish oily residue is purified by distillation (boiling point: 98–102° C./0.05 bar). Yield: 38.9 g (90%, colourless liquid); purity ee-product (HPLC, OD-H, hexane/ethanol/TFA: 970/30/0.4 ml): 99%.

EXAMPLE 2

5.0 mg of MeOHCd (O-methoxy-10,11-dihydrocinchonidine) are placed in a 50 ml stainless steel autoclave, equipped with double-walled jacket, magnetic stirrer and baffles. 50 mg of 5% PtAl$_2$O$_3$ (JMC 94, pretreated for 2 h in H$_2$ at 400° C.) are added and the mixture is suspend in 5 ml of EtOH and in 2.0 g of 5 (C$_4$H$_4$O$_5$, MG 132.07) dissolved in 20 ml of EtOH. The autoclave is closed and rinsed three times each with argon and with hydrogen. The pressure is then raised to 60 bar H$_2$ and the reaction is started by stirring with the magnetic stirrer. After reacting for 160 min and relaxing, the autoclave is rinsed with argon. The reaction mixture is filtered and EtOH is removed by evaporation, giving 2.04 g of 6 [C$_4$H$_6$O$_5$, MG 134.08: yield: 100%; ee-product=62% (HPLC)].

EXAMPLE 3

0.72 g of 8 [C$_8$H$_{14}$O$_5$, MG 190.20; yield: 89% ee-product: 70% (HPLC)] is prepared in analogy to Example 2 by hydrogenating 0.8 g of 7 (C$_8$H$_{12}$O$_5$, MG 188.18) in 5.0 mg of HCd (10,11-dihydrocinchonidine).

EXAMPLE 4

The compounds 10, 12, 14 can be prepared in analogy to Example 2 by hydrogenating 9, 11, 13 using HCd as chiral modifier in ethanol or toluene as solvent:

[12: NMR:1.16 ppm (s, 9H, CH$_3$), 1.30 ppm (t, 3H, CH$_3$), 3.02 ppm (d, 2H, CH$_2$), 3.24 (d, 1H, OH), 4.25, (q, 2H, CH$_2$), 4.46 (dd, 1H, CH)]

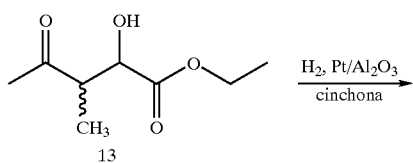

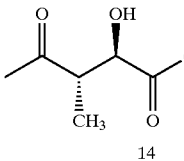

ee 70/63
anti/syn 12/1

EXAMPLE 5

A 50 ml micro-autoclave is charged with 126.5 mg of 5% Pt—SiO2 (Heraeus B 98/15) and 14.1 mg of dihydrocinchonidine. Subsequently, 4.98 g of diketo ester (1, 5, 9, 11, 13 as 20% solution in toluene) are added. The autoclave is closed and rinsed three times each with 10 bar argon and 10 bar hydrogen. The hydrogen pressure in the autoclave is adjusted to 40 bar and the valve is closed. The reaction is started by switching on the stirrer. During hydrogen uptake, the temperature in the vessel rises from 22° C. to 28° C. After about half an hour, the pressure in the vessel must be raised again to about 40 bar because it has sunken to about 20 bar through the hydrogen consumption. After three hours the reaction is stopped and the hydrogenation mixture is filtered off from the catalyst and analysed (HPLC on chiral column). A reaction of 100% at an ee of 74% is found.

What is claimed is:

1. A process for the preparation of a compound of formulae

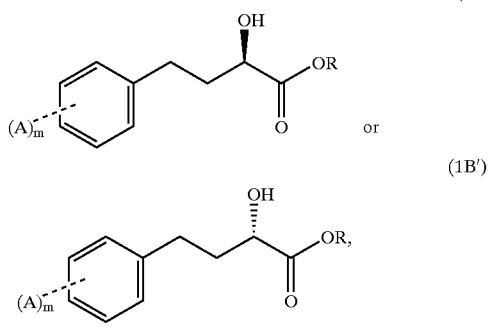

wherein

A is $C_1$–$C_7$alkyl, $C_1$–$C_7$alkoxy, $C_1$–$C_4$alkanoyl, $C_1$–$C_4$alkanoyloxy, cyanogen, halogen, hydroxy, carboxy, $C_1$–$C_4$alkoxycarbonyl, $C_1$–$C_7$alkylenedioxy, amino, $C_1$–$C_4$alkylamino, di($C_1$–$C_7$alkyl)amino, $C_1$–$C_4$alkanoylamino, carbamoyl, $C_1$–$C_4$alkylcarbamoyl, di($C_1$–$C_7$alkyl)carbamoyl, $C_1$–$C_4$alkanesulfonylamino, arenesulfonylamino, sulfo, sulfamoyl, $C_1$–$C_4$alkylsulfamoyl, di($C_1$–$C_7$alkyl)sulfamoyl, halogen-$C_1$–$C_7$alkyl, hydroxy-$C_1$–$C_7$alkyl or amino-$C_1$–$C_7$alkyl, m is an integer from 0 to 5 and R is $C_1$–$C_{20}$alkyl, $C_3$–$C_{12}$cycloalkyl, tetrahydrofuryl, pyrrolidinyl, piperazinyl, tetrahydrothienyl, phenyl, naphthyl, furyl, thienyl, pyrrolyl, pyridyl, pyrimidinyl or benzyl, each of which is unsubstituted or substituted by one or more than one substituent selected from the group consisting of $C_1$–$C_6$alkyl, $C_1$–$C_6$alkoxy, $C_1$–$C_6$haloalkyl, phenyl, naphthyl, carboxy, $C_1$–$C_4$alkoxycarbonyl, $C_1$–$C_4$alkanoyl, —$SO_3^-$, ammonium and halogen, which comprises enantioselectively hydrogenating an α,γ-diketo ester of formula

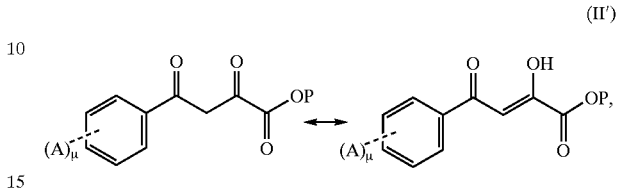

wherein A, m and R have the cited meanings, or the tautomer thereof, with platinum as catalyst in the presence of a cinchona alkaloid as chiral modifier, and hydrogenating one of the obtainable compounds of formulae

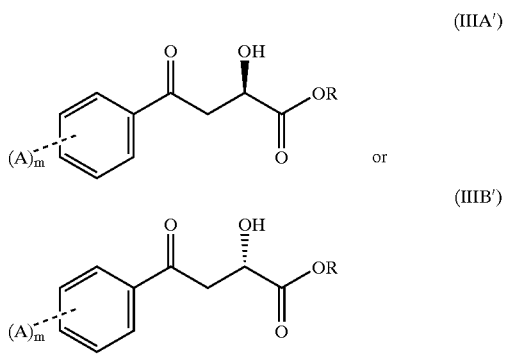

having the desired configuration with palladium as catalyst.

2. A process according to claim 1 for the preparation of a compound (I A') or (I B'), wherein A is $C_1$–$C_7$alkyl, $C_1$–$C_7$alkoxy, $C_1$–$C_4$alkanoyl, $C_1$–$C_4$alkanoyloxy, cyanogen, halogen, hydroxy, carboxy, $C_1$–$C_4$alkoxycarbonyl, $C_1$–$C_7$alkylenedioxy, amino, $C_1$–$C_4$alkylamino, di($C_1$–$C_7$alkyl)amino, $C_1$–$C_4$alkanoylamino, carbamoyl, $C_1$–$C_4$alkylcarbamoyl, di($C_1$–$C_7$alkyl)carbamoyl, $C_1$–$C_4$alkanesulfonylamino, arenesulfonylamino, sulfo, sulfamoyl, $C_1$–$C_4$alkylsulfamoyl, di($C_1$–$C_7$alkyl)sulfamoyl, halogen-$C_1$–$C_7$alkyl, hydroxy-$C_1$–$C_7$alkyl or amino-$C_1$–$C_7$alkyl, m is an integer from 0 to 5 and R is $C_1$–$C_{20}$alkyl, $C_3$–$C_{12}$cycloalkyl, tetrahydrofuryl, pyrrolidinyl, piperazinyl, tetrahydrothienyl, phenyl, naphthyl, furyl, thienyl, pyrrolyl, pyridyl, pyrimidinyl or benzyl, each of which is unsubstituted or substituted by one or more than one substituent selected from the group consisting of $C_1$–$C_6$alkyl, $C_1$–$C_6$alkoxy, $C_1$–$C_6$haloalkyl, phenyl, naphthyl, carboxy, $C_1$–$C_4$alkoxycarbonyl, $C_1$–$C_4$alkanoyl, —$SO_3^-$, ammonium and halogen, which process comprises hydrogenating a compound (III A') or (III B') having the desired configuration with palladium as catalyst.

3. A process according to claim 1 for the preparation of a compound (III A') or (III B'), wherein A is $C_1$–$C_7$alkyl, $C_1$–$C_7$alkoxy, $C_1$–$C_4$alkanoyl, $C_1$–$C_4$alkanoyloxy, cyanogen, halogen, hydroxy, carboxy, $C_1$–$C_4$alkoxycarbonyl, $C_1$–$C_7$alkylenedioxy, amino, $C_1$–$C_4$alkylamino, di($C_1$–$C_7$alkyl)amino, $C_1$–$C_4$alkanoylamino, carbamoyl, $C_1$–$C_4$alkylcarbamoyl, di($C_1$–$C_7$alkyl)carbamoyl, $C_1$–$C_4$alkanesulfonylamino, arenesulfonylamino, sulfo, sulfamoyl, $C_1$–$C_4$alkylsulfamoyl, di($C_1$–$C_7$alkyl)sulfamoyl, halogen-$C_1$–$C_7$alkyl, hydroxy-$C_1$–$C_7$alkyl or amino-$C_1$–$C_7$alkyl, m is an integer from 0 to 5 and R is $C_1$–$C_{20}$alkyl, $C_3$–$C_{12}$cycloalkyl, tetrahydrofuryl, pyrrolidinyl, piperazinyl, tetrahydrothienyl, phenyl, naphthyl, furyl, thienyl, pyrrolyl, pyridyl, pyrimidinyl or benzyl, each of which is unsubstituted or substituted by one or more than one substituent selected from the group consisting of $C_1$–$C_6$alkyl, $C_1$–$C_6$alkoxy, $C_1$–$C_6$haloalkyl, phenyl, naphthyl, carboxy, $C_1$–$C_4$alkoxycarbonyl, $C_1$–$C_4$alkanoyl, —$SO_3^-$, ammonium and halogen, which comprises enantioselectively hydrogenating a compound (II') with platinum as catalyst in the presence of a cinchona alkaloid and, if required, enriching the obtainable compound (III A') or (III B') with the desired configuration.

4. A compound of formulae

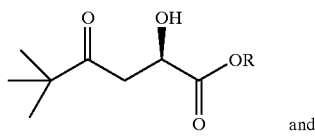

(IIIA")

and

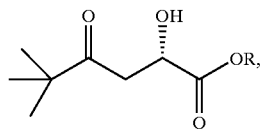

(IIIB")

wherein R is $C_1$–$C_{20}$alkyl, $C_3$–$C_{12}$cycloalkyl, tetrahydrofuryl, pyrrolidinyl, piperazinyl, tetrahydrothienyl, phenyl, naphthyl, furyl, thienyl, pyrrolyl, pyridyl, pyrimidinyl or benzyl, each of which is unsubstituted or substituted by one or more than one substituent selected from the group consisting of $C_1$–$C_6$alkyl, $C_1$–$C_6$alkoxy, $C_1$–$C_6$haloalkyl, phenyl, naphthyl, carboxy, $C_1$–$C_4$alkoxycarbonyl, $C_1$–$C_4$alkanoyl, —$SO_3^-$, ammonium and halogen with the exception of methyl.

5. 5,5-dimethyl-(R)-2-hydroxy-4-oxohexanoic acid ethyl ester according to claim 4.

* * * * *